United States Patent [19]
Borghi

[11] Patent Number: 6,051,001
[45] Date of Patent: Apr. 18, 2000

[54] DEVICE AND METHOD FOR MOUNTING AN ENDOVASCULAR STENT ONTO A BALLON CATHETER

[75] Inventor: Enzo Borghi, Budrio, Italy

[73] Assignee: AVE Galway Limited, Galway, Ireland

[21] Appl. No.: 09/011,637

[22] PCT Filed: Sep. 10, 1996

[86] PCT No.: PCT/IB96/00918

§ 371 Date: Feb. 13, 1998

§ 102(e) Date: Feb. 13, 1998

[87] PCT Pub. No.: WO97/09946

PCT Pub. Date: Mar. 20, 1997

[51] Int. Cl.[7] .................................................. A61F 11/00
[52] U.S. Cl. .......................................... 606/108; 606/198
[58] Field of Search .................................. 606/108, 191, 606/195, 198, 194

[56] References Cited

U.S. PATENT DOCUMENTS

| | | |
|---|---|---|
| 4,649,922 | 3/1987 | Wiktor . |
| 5,342,300 | 8/1994 | Stefanadis et al. ..................... 606/198 |
| 5,702,419 | 12/1997 | Berry et al. .............................. 606/198 |

FOREIGN PATENT DOCUMENTS

| | | |
|---|---|---|
| 0540290 | 5/1993 | European Pat. Off. . |
| 0630623 | 12/1994 | European Pat. Off. . |
| 0697226 | 2/1996 | European Pat. Off. . |
| 3640745 | 11/1986 | Germany . |
| WO9520992 | 8/1995 | WIPO . |
| WO9526777 | 10/1995 | WIPO . |
| WO9609013 | 3/1996 | WIPO . |
| WO9641591 | 12/1996 | WIPO . |

*Primary Examiner*—Michael Buiz
*Assistant Examiner*—Kevin Truong
*Attorney, Agent, or Firm*—Sterne, Kessler Goldstein & Fox PLLC

[57] ABSTRACT

A method for securely mounting an endovascular stent (2) to a balloon catheter (3, 5) involves the use of a loading device (1) that includes a longitudinal sheath having an opening (10) into which the balloon (5) is inserted. The stent is supported slidably along the outside of the sheath so that it can be slid along the sheath into a position coaxially about the balloon. The stent then is released into stable and secure engagement with the balloon (5) by withdrawing the sheath from between the stent and the balloon. The method may be used in conjunction with a stent that is elastically deformable to a diameter enabling it to be placed about the balloon and then permitted to tighten, elastically, into secure engagement with the balloon, gradually and uniformly. The sheath may be in the form of longitudinal elements (7) connected at one end to a support (6) and having free opposite ends.

22 Claims, 2 Drawing Sheets

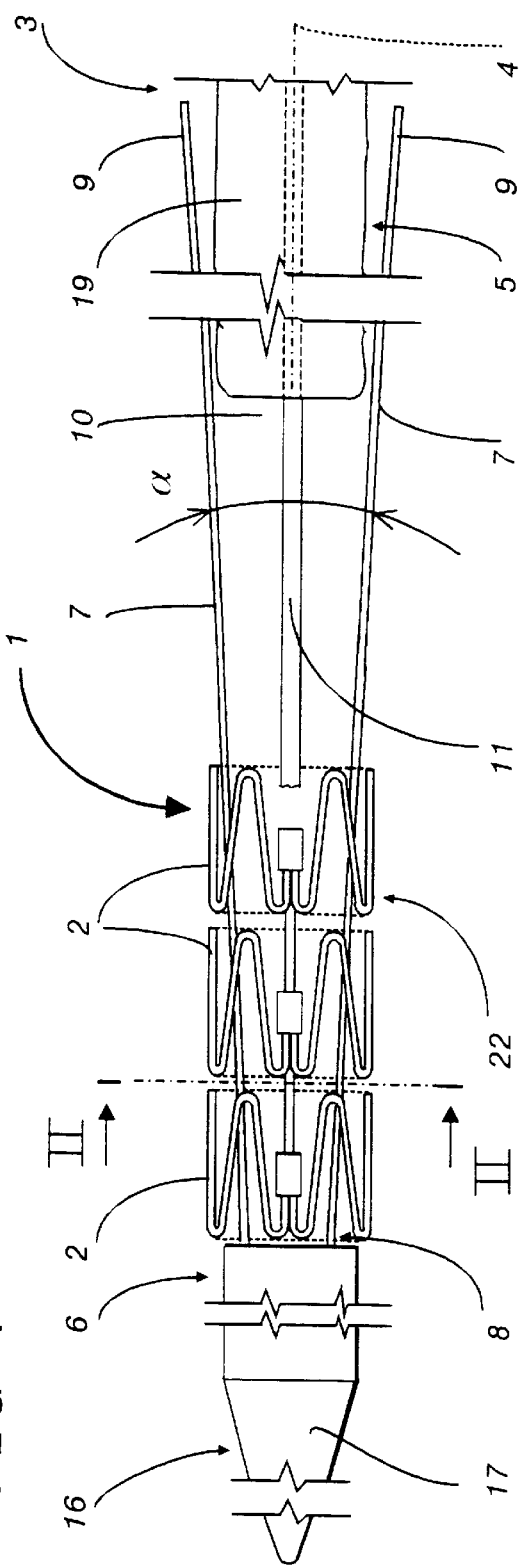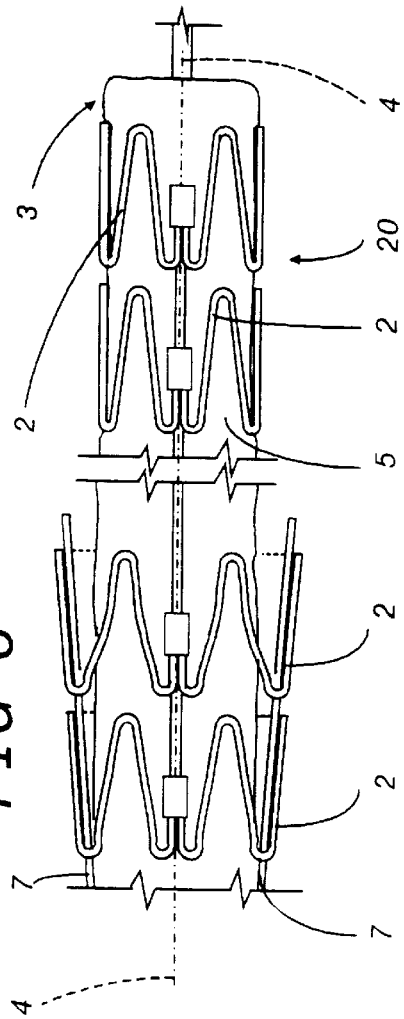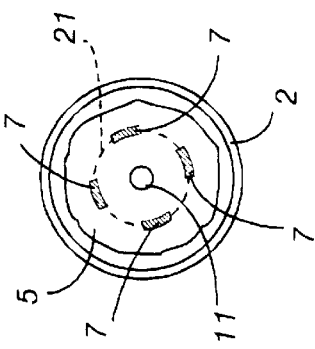

DEVICE AND METHOD FOR MOUNTING AN ENDOVASCULAR STENT ONTO A BALLON CATHETER

TECHNICAL FIELD

The invention relates to devices and techniques for mounting an endovascular stent onto the balloon of a delivery catheter to enable the catheter to deliver and deploy the stent in a body lumen such as a coronary or peripheral blood vessels.

BACKGROUND OF THE INVENTION

Among the techniques currently employed in connection with dilatation of a body lumen, such as a blood vessel that has become restricted by pathological or traumatic occurrence, has been to place an endovascular stent within the dilated region of the vessel, in order to maintain the vessel patient. One technique for placing such an endovascular stent has been to mount the stent onto a folded balloon of a balloon catheter and then insert and advance the stent and catheter together into the body lumen to locate the stent at the intended site of implantation. So located, the balloon then is inflated to expand the stent into engagement with the vessel wall to stabilize the position of the stent within the lumen. The procedure requires first that the stent be properly located on the balloon and second, that it be secured to the balloon to assure it will remain in place during the placement procedure.

Positioning the stent on the balloon has involved selection of a stent having an initial internal diameter greater than the radial dimensions of the folded balloon and the catheter to enable the stent to be slipped over the catheter and about the balloon. The stent then is constricted radially about the balloon and catheter by means of pincers or other crimping tools to inelastically deform the stent to a smaller diameter in which the stent maintains a firm grip on the folded balloon.

The foregoing technique for securing an endovascular stent to the balloon of the catheter presents a number of difficulties. The balloon typically is formed from a very thin, membranous material that is susceptible to damage, either by the stent rubbing against the folds of the balloon when the stent is positioned along the balloon or by excessive crimping pressure when the stent is constricted tightly about the balloon. Crimping the stent onto the balloon necessarily is empirical and difficult to control. Additionally, some stents are formed employing a laser cutting procedure in which edges of the stent may be insufficiently rounded thereby presenting increased risk of damage when crimped about the balloon. Moreover, once the stent is crimped onto the balloon it may not be possible to detect the presence of such damage. Consequently, there may be increased risk that the balloon will burst during inflation with potentially life threatening consequences to the patient.

Also, among the difficulties with the above-described technique for mounting a stent onto a balloon catheter is that because of the uncertainties in the use of the crimping technique, the stability of the position of the stent on the balloon may be compromised. When a catheter is advanced along a body lumen it can be expected to encounter deviations, bends, or restrictions resulting either from the natural anatomy of the lumen or by the presence of atherosclerotic plaque, any of which may cause the stent to slip from its initial position on the balloon. Additionally, the shifting of the stent on the balloon may result in the stent snagging the balloon, causing undetected damage that, in turn, can present difficulties in localizing and stabilizing the stent at its intended placement site. Even if slipping of the stent on the balloon is detected, it can be expected to further lengthen the duration of the procedure. Most seriously, the stent possibly could become irretrievably separated from the balloon inside the patient's body, thereby presenting significant risk to the patient.

DISCLOSURE OF THE INVENTION

It is among the primary objects of the invention to provide a device and technique by which a stent can be fitted onto the balloon of a delivery catheter with minimal risk of damaging the balloon. Another object of the invention is to provide a device and technique by which the stent can be secured in a stable position on the balloon to prevent relative movement of the stent along the balloon when the two are advanced together into and through the body lumen.

These objects are realized by the use of a stent loading device that includes elongate elements defining an elongate sheath having opposed ends. One end of the sheath is arranged to extend through and support the endovascular stent in readiness and in a manner that enables the stent to be slid along the axis of the sheath toward the opposite end. The opposite end of the sheath is arranged to be open to receive and embrace the balloon with the axes of the sheath, balloon and stent being aligned. So juxtaposed, the stent then can be slid along the sheath toward the opposite end of the sheath to a position about the balloon while the balloon is protectively embraced within the sheath. The balloon thus is protected from sliding engagement by the stent as the stent is slid into position about the balloon. When the longitudinal position of the stent and balloon are as desired, the relative position of the stent and the balloon is maintained while the sheath is slid from between the stent and the balloon, leaving the stent in place on and in engagement with the balloon.

Another aspect of the invention relates to the manner in which the stent remains in a secure and stable position on the balloon so that relative movement between the stent and the balloon is prevented when the two are advanced into the body lumen. To that end, the invention is used in conjunction with an endovascular stent that is constructed to be elastically deformable in a radial direction within a limited range of radial expansion and contraction. In this aspect of the invention, the stent loading device includes elongate sheath-defining elements that extend through the stent and apply a radially outward force to the stent as the stent is slid towards the free end of the sheath and about the balloon. The radial expansive force applied by the sheath elements causes the stent to expand circumferentially as it advances from one end of the loading device to the other, enabling it to widen to a diameter greater than that of the folded balloon but within the range of elastic expansion and contraction permitted by the stent. By expanding elastically, the stent will store elastic energy such that when the sheath is subsequently removed, that elastic energy will cause the stent to itself contract, unassisted, about the balloon to lock itself stably about and onto the balloon. Thus, the present invention may be employed to load a stent onto a balloon in a manner that enables the stent to crimp itself to the balloon. In addition, to affording increased security against the risk of inadvertent separation between the stent and the balloon, the self-crimping action provides uniform distribution of the gripping force of the stent along the length of the balloon. The uniform distribution of the gripping force is maintained even when the balloon and the catheter are deformed as they are advanced through the patient's vessels. The arrangement enables the physician to secure a variety of stents to a variety of balloon catheters to enable the device and technique to be applied to a wide variety of different clinical situations. Additionally, because of the effectiveness with which the self-crimping stent engages the balloon, the duration of the procedure may be reduced significantly.

Also, among the objects of the invention is to provide a device for loading an endovascular stent onto a balloon catheter that is easy to manufacture and use and lends itself to preassembled stent and loading devices.

DESCRIPTION OF THE DRAWINGS

The foregoing and other objects and advantages of the invention will be appreciated more fully from the following example, with the aid of the accompanying drawings in which:

FIG. 1 provides an overall view of a device according to the present invention, seen partly fragmented and enlarged from its actual size and in association with an inflatable balloon catheter;

FIG. 2 is a cross-sectional view of the device illustrated in FIG. 1, taken along the plane II—II of FIG. 1;

FIG. 3 is a combined illustration showing the stent and loading device in two configurations relative to the balloon, including one configuration (to the right) in which a portion of the stent is shown in engagement with the balloon after the loading device has been withdrawn, and another configuration (to the left) in which a portion of the stent has been expanded elastically by the sheath in readiness to effect a self-crimping engagement with the balloon;

DESCRIPTION OF THE ILLUSTRATIVE EMBODIMENT

Figure 5:
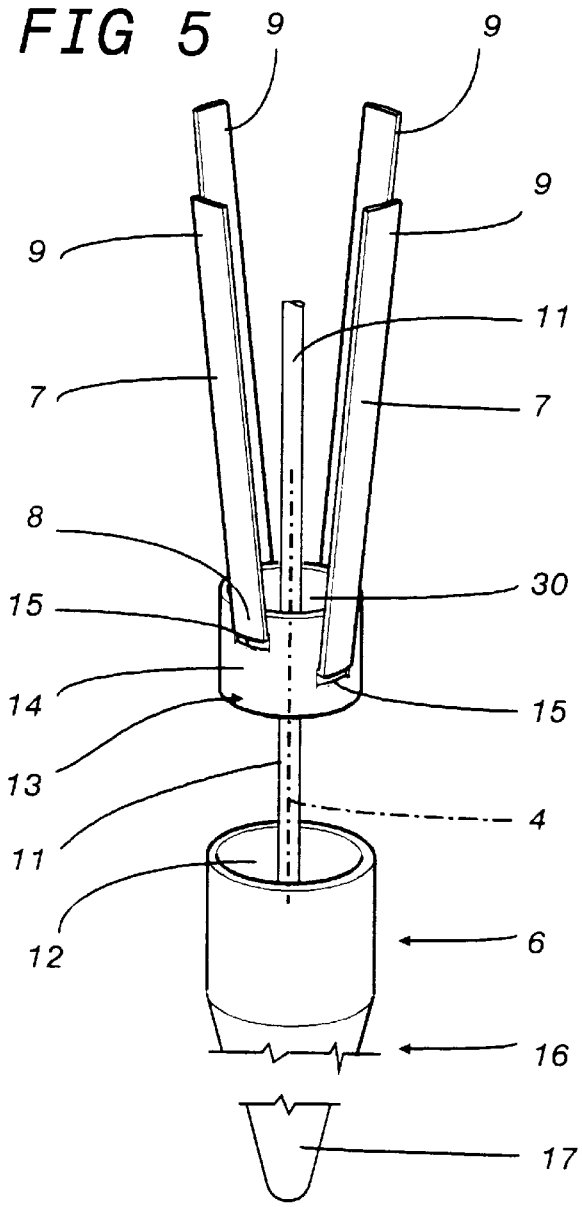
FIG. 5 shows a preferred embodiment of a loading device according to the invention in an exploded perspective view, illustrated schematically and with certain parts omitted for clarity of illustration.

As shown in FIG. 1, the loading device, indicated generally at 1, is employed to mount an endovascular stent 2 onto an inflatable balloon 5 of a catheter 3 with the stent, balloon and catheter being disposed coaxially about an axis 4. When the stent 2 has been loaded onto the balloon 5 of the catheter, the assembly can be inserted into the body vessel and can be advanced in an axial direction 4 within the lumen of the vessel.

In the following description, the term "distal" will refer to a direction that is toward the patient and the term "proximal" will refer to a direction along the axis 4 that is away from the patient, e.g., toward the physician. Thus, the end of the balloon catheter to which the balloon is attached may be considered as the distal end and the end of the catheter that remains outside of the patient and is operated by the physician is the proximal end of the catheter.

The device includes an arrangement that forms a sheath having means adapted to embrace the balloon to protect the balloon while the endovascular stent 2 is slid in a proximal direction along the axis 4 to a desired longitudinal position along and about the balloon. So positioned, the sheath then can be slidingly withdrawn, in a distal direction, from between the balloon and the stent, leaving the stent in place on the balloon. In the illustrative example of the invention, the loading device 1 may comprise a support 6 and a plurality (e.g., four) longitudinal sheath-defining fingers 7 having distal ends 8 and proximal ends 9. The sheath may be considered to define a first means at the distal portion of the sheath for supporting the stent 2 in a preload condition and a second means at the opposite, proximal ends 9 of the sheath-defining fingers 7 arranged to define a space 10, receptive to the balloon. The fingers 7 are connected securely at their distal ends 8 to the support 6. The elongate sheath-defining fingers 7 may be generally lamellar, being flat or arcuate in cross-section to coincide with a circumferential arc (FIG. 2) about which the fingers 7 are uniformly and equidistantly distributed. In the illustrative embodiment, the support 6 includes a stent guide 16 having a tapered distal end 17 to facilitate preliminary placement of the stent 2 on the elongate sheath-defining fingers 7. The support 6 also can include a proximally extending stylet 11 that can be inserted into the lumen of the balloon catheter 3 to axially align the loading device 1 with the catheter so that the balloon 5 can be guided into the space 10 embraced by the fingers 7 as well as to provide added support for the balloon region of the catheter during the loading process. The distal end of the stylet 11 may be secured to the stent support 6.

As shown in FIG. 5, the illustrative embodiment of the support 6 includes an internal cavity 12 that receives a smaller diameter tubular element 13 having a peripheral wall 14 in which four openings 15 are formed. The openings 15 are arranged in two pairs, spaced longitudinally along the axis 4 and displaced circumferentially at 90°, one from the next. The longitudinal sheath-defining fingers 17 may be formed from two elongate metal strips, one associated with each pair of openings 15, with each strip being passed through one pair of openings 15 with its ends extending freely away from the support 6. The tubular element 13 with the longitudinal fingers 7 attached, then can be inserted into the cavity 12 of the support 6 thereby to stably secure the element 7 between the tubular element 13 and the support 6.

The device may be manufactured by a method that includes the steps of (1) removing material, as by milling, from a peripheral wall 14 of a tubular element 13 to form at least two opposed openings 15, (2) fitting at least one longitudinal finger 7 to the tubular element 13 by insertion through the openings 15, (3) coupling the tubular element 13 with the internal cavity 12 of the support 6 so that the longitudinal fingers 7 remain stably anchored between the tubular element 13 and the support 6. The foregoing construction is simple and economically achieved at low cost thereby lending itself to disposable use. Advantageously, the loading device may be supplied to the physician in combination with a preassembled stent 2, thereby further simplifying the procedure for the physician and reducing the duration of the implantation procedure.

In the preferred embodiment, the fingers 7 are connected to and project from the support 6, to diverge at an angle α in a proximal direction. When the stent 2 is assembled with the loading device, the stent 12 is placed over the tapered portion 17 of the guide element and is advanced longitudinally to a location encircling a distal portion of the fingers 7 adjacent the distal ends 8. At this point, the stent will be supported internally by the fingers 7 that engage the stent 2 from within. When the stent 2 is later advanced proximally toward the free ends 9 of the fingers 7, the divergent fingers 7 will apply a radially outward force to the stent to enlarge the diameter of the stent, within its elastic limit, to a degree that will allow the stent to be positioned coaxially about the balloon 5. The outer diameter of the tubular support 6 preferably is greater than the inside diameter of the stent when the stent is relaxed. The support 6 may have an outer diameter approximately 10% greater than the inside diameter of the relaxed stent so that when the stent is advanced over the support 6, the stent will stretch elastically and radially. The effective diameter of the distal portion of the sheath is less than that of the support 6 so that after the stent has been passed over the support 6, it will elastically contract toward its relaxed configuration. Thereafter, the larger diameter of the support 6 serves to retain the stent in its position about the sheath-defining fingers 7 thereby retaining the stent in place on the loading device and in readiness to be loaded onto the balloon.

The divergent orientation of the fingers 7 also defines a convergent end of the balloon-receptive space 10 that can serve to limit the extent to which the balloon can be inserted axially into the space 10. Therefore, by selecting a suitable correlation between the length of the sheath-defining fingers 7, their angle of convergence α and the length and the dimensions of the folded balloon 5, the extent to which the catheter and balloon can advance into the space 10 can be limited so that a trailing portion 19 of the balloon will be exposed beyond the trailing end of the elements 7, just sufficiently to be engaged by a corresponding end 20 of the stent 2.

When the stent 2 and loading device 1 have been assembled, the stent will be disposed on and about the fingers 7 at a distal region of the sheath, adjacent the support 6, with the free ends 9 of the fingers 7 extending proximally beyond the stent 2 in a divergent array. So configured, the balloon at the distal end of the catheter is advanced into the receptive space 10 and may be guided in that movement by cooperation of the stylet 11. When the catheter and loading device have been engaged, with the balloon 5 of the catheter being embraced by the sheath-defining fingers 7, the stent 2 can be advanced proximally along the fingers 7 to a desired longitudinal position about the balloon. So positioned, the stent may be held in place relative to the balloon and the loading 1 device can be removed. As the loading device is withdrawn from between the stent and the balloon, the stent will engage the balloon. Thus, the stent can be loaded onto and positioned on the balloon while the balloon is protectively embraced by the sheath and protected from damage by the stent. The balloon-engaging surfaces of the lamellar fingers 8 can slide smoothly over the balloon without injury to the balloon.

Figure 4:
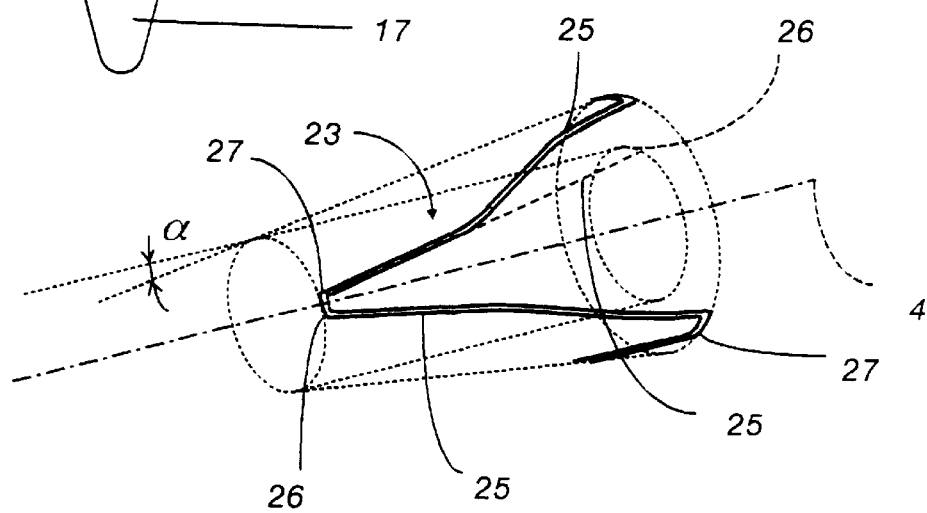
FIG. 4 illustrates, in perspective, a portion of a tubular stent formed from wire illustrating the manner in which that stent may flex elastically in readiness to self-crimp onto the balloon.

The invention can be used with particular advantage with an endovascular stent that can be deformed elastically within a range sufficient to enable the stent to be elastically expanded to a diameter to facilitate its placement over the balloon and then permitted to elastically contract into self-crimping engagement with the balloon. One such stent is illustrated in FIG. 4 and is described in further detail in PCT Patent Application No. PCT/IB96/00568, the disclosure of which is hereby incorporated by reference, in its entirety. The stent 2 comprises a series of tubular modules 23. Individual modules are connected to a spine that extends longitudinally of the axis 4. The modules 23 are constructed by fashioning a metal wire substantially into a serpentine configuration that defines elongate, longitudinally extending straight portions 25 alternated with shorter portions 26 disposed transversely to the axis 4. The substantially straight longitudinal portions 25 and transverse portions 26 are connected by segments 27 of wire permanently bent to an angle that will provide rigidity and enable the module 23 to withstand action applied transversely to the axial direction 4 intending to vary the width of the angle. The straight segments 25 have elastic properties and can be likened to a series of beams anchored at the ends to movable restraints provided by the bent portions of wire 27. The stent 2 thus may be considered to define a relaxed diameter and can be elastically expanded from its relaxed diameter within a limited range of diameters sufficient to enable the stent to be loaded onto the loading device and then, from the loading device onto and about the folded balloon. When the stent is deployed, however, it may be expanded to a diameter greater than the limited elastic range, in which case the stent will be elastically deformed.

As the stent 2 is slidably advanced along the elongate element 7, the individual modules 27 will tend to expand in diameter. By selecting the angle of divergence α and the dimensions of the longitudinal elements, the angle of the bent portions 27 of the wire can remain constant as the stent 2 is slid along the device and the stent 2 expands. Thus, the increase in the circumference of the module 23 is attributable to the elastic deformability of the elongate segments 25 of the stent, which are able to deflect from a straight, undeformed configuration to a bent, deformed configuration, as illustrated in FIGS. 3 and 4. The elastic deformation of the straight segments 25 is reversible and, therefore, as the stent advances to and beyond the free ends 9 of the fingers 7, the segments 25 of the stent 2 return immediately and elastically to their straight, undeformed configuration. Consequently, as the modules 23 at the restraining end 20 of the stent 2 are separated progressively from the fingers 7, they will contract elastically and tighten firmly around the portion 19 of the balloon 5 disposed beyond the free ends 9 of the fingers 7 and beyond the space 10 (FIG. 3). As the retraction of the loading device 1 progresses along the axial direction 4, the complete set of modules will be transferred progressively onto the balloon until the stent 2 is ultimately positioned and has self-crimped uniformly and stably to and about the balloon. The foregoing occurs without any relative sliding contact between the stent 2 and the balloon 5 in the axial direction 4 and without inelastically crimping the stent onto the balloon.

It should be noted that the elasticity of the modules 23 depends to an extent on the properties of the materials used and manufactured and on the geometry of the modules 23 themselves, as well as on the angle of divergence α and on the length of the longitudinal element 7. As to relative proportions, satisfactory results appear to be achieved when the length of the elongate fingers 7 is about twice the length of the stent 2.

Figure 6:
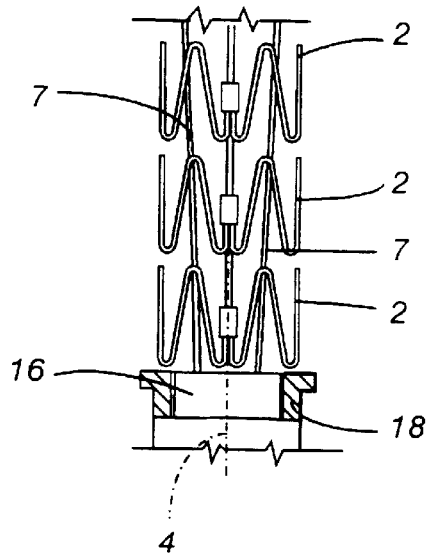
FIG. 6 shows the device according to the invention in part and in an alternative embodiment.

The stent thus can be fitted manually to the catheter by the physician directly and at the time of the operating procedure. Stents of a moderate length (e.g., about 15 to 25 mm) can be fitted manually to the catheter by the physician with ease. Should the loading of a longer stent (e.g., about 25 to 35 mm) present some difficulty in handling, especially when the physician is wearing gloves, the loading device 1 may also incorporate a push member 18 slidably associated with the guide element 16 and engageable with an end of the stent 2 as indicated in FIG. 6.

From the foregoing it will be appreciated that the invention provides an improved method for fitting an endovascular stent 2 onto the balloon 5 in which a protective sheath is provided over and about the folded balloon to enable a stent, positioned outside of the sheath, to be slid along the sheath into a position about and coaxial with the balloon and withdrawing the sheath in a direction opposite that of the sliding movement of the stent, to draw the sheath from between the balloon and the stent. In a further aspect of the method, the sheath is arranged to apply a radial expansive force to the stent to elastically enlarge the diameter of the stent so that it can be advanced over the balloon. With the stent in position about the balloon, the radial expansive force is removed to enable the stent to resiliently constrict about the balloon without requiring application of external crimping forces.

From the foregoing, it will be appreciated that the objects of the invention are fully realized and provide greater reliability, lower costs and increased safety. It should be understood, however, that the foregoing description of the invention is intended merely to be illustrative thereof and that other embodiments, modifications and equivalents may be apparent to those skilled in the art without departing from its principals.

What is claimed is:

1. A device for loading a balloon-expandable elongate tubular stent having a selected length on a balloon of a catheter insertable into a body vessel comprising:

an elongate sheath having a distal end and a proximal end, said elongate sheath being longer than the selected length and divergent toward the proximal end thereof, wherein the distal end of the sheath is adapted to be received within the stent and the proximal end of the sheath extends freely beyond the stent such that the sheath applies a radially outward force to elastically expand the stent as the stent is slid from the distal end to the proximal end thereof and wherein an open space is formed in the proximal end of the sheath receptive to the balloon of the catheter.

2. A stent loading device as defined in claim 1 wherein the sheath comprises:

at least two longitudinally extending fingers connected together at a location to define the first end of the sheath.

3. A stent loading device as defined in claim 2 further comprising:

the first end of the sheath being attached to a support.

4. A stent loading device as defined in claim 3 further comprising:

the support defining an internal cavity;

a tubular member having a peripheral wall and at least two openings;

the longitudinal fingers passing through the openings; and the tubular member being received in the internal cavity of the support to securely anchor the longitudinal fingers by capturing the fingers between the tubular element and the support.

5. A stent loading device as defined in claim 3 further comprising an axially extending guide element having a first end and a second end wherein the first end of the guide element is supported at the distal end of the sheath and the second end of the guide element extends axially and is engageable with the catheter to axially align the balloon with the proximal end of the sheath.

6. A stent loading device as defined in claim 3 wherein the support comprises a guide element to facilitate advancement of the stent onto the longitudinal fingers.

7. A stent loading device as defined in claim 6 wherein the guide element (16) has a tapered portion (17).

8. A stent loading device as defined in any one of claims 1 or 2 wherein the length of the sheath is approximately twice that of the stent with which the sheath is to be used.

9. A stent loading device as defined in any one of claims 1, 2 or 8 further comprising an axially extending guide element having a first end and a second end wherein the first end of the guide element is supported at the distal end of the sheath and the second end of the guide element extends axially and is engageable with the catheter to axially align the balloon with the proximal end of the sheath.

10. A stent loading device as defined in claim 9 wherein the longitudinal fingers (7) are generally lamellar.

11. A stent loading device as defined in claim 10 wherein the lamellar fingers (7) are flat in cross-sectional profile.

12. A stent loading device as defined in claim 10 wherein the lamellar fingers (7) are arcuate in cross-sectional profile.

13. A stent loading device as defined in claim 1 wherein the length and angle of divergence of the sheath are correlated to the length and diameter of the balloon such that when the balloon is inserted into the space at the second end of the sheath, the balloon will present a portion protruding beyond the second end of the sheath sufficiently to provide a surface of the balloon adapted to be gripped by an end of the stent.

14. A stent loading device as defined in claim 2 or 6 further comprising a pushing member slidably mounted with respect to the guide and engageable with the stent.

15. A stent loading device as defined in claim 2 wherein there are four longitudinal fingers (7).

16. A stent loading device as defined in claim 2 wherein the fingers (7) are formed from metal.

17. A stent loading device as defined in claim 2 wherein the fingers (7) are arranged to be circumferentially spaced at substantially mutually equidistant intervals.

18. A device for loading a balloon-expandable elongate tubular stent on a balloon of a catheter insertable into a body vessel comprising:

first means for engagement with the interior of the tubular stent for supporting the stent in a preloaded condition;

second means formed as a continuation of the first means for receiving and embracing tie balloon therein and applying a radially outward force to elastically expand the stent when the stent is slid thereon;

whereby the loading device may serve as a guide to enable sliding transfer of the stent from the first means to the second means thereby disposing the stent about the balloon;

the second means being removable from between the stent and the balloon to enable transfer of the stent to the balloon while avoiding direct sliding contact of the stent with the balloon.

19. A stent loading device as defined in claim 18 wherein at least the second means further includes means for applying a radially outward force to the interior of the stent as the stent is advanced along the second means.

20. A stent loading device as defined in either of claims 1 or 18 further in combination with a stent mounted on the loading device, the stent and loading device being preassembled in readiness for transfer of the stent from the loading device to the balloon.

21. A stent loading device and stent, combined as defined in claim 20 wherein the stent further comprises:

a plurality of tubular modules (23) connected relative to each other in axial array along a spine.

22. A device as in either of claims 1 or 18, packaged together with a modular endovascular stent as a preassembled vascular implant delivery system.

* * * * *

UNITED STATES PATENT AND TRADEMARK OFFICE
CERTIFICATE OF CORRECTION

PATENT NO. : 6,051,001

DATED : April 18, 2000

INVENTORS : Borghi, Enzo

It is certified that an error appears in the above-identified patent and that said Letters Patent is hereby corrected as shown below.

On the title page:
In the title, "Ballon" should be --Balloon--;

Title page of the patent the following priority data should appear:

--[30] Foreign Application Priority Data
Sept. 13, 1995 [IT]         Italy  . . . . . . . . . . . . . . . . . . . . . . . . B095 A 000430--;

In column 1, line 3, "Ballon" should be --Balloon--;

In column 7, line 38, "first" should be --distal--;

In Column 8, line 15, "second" should be --proximal--;

In Column 8, line 36, "tie" should be --the--.

Signed and Sealed this

Twenty-second Day of May, 2001

*Attest:*

NICHOLAS P. GODICI

*Attesting Officer*    Acting Director of the United States Patent and Trademark Office